(12) United States Patent
Rudnick et al.

(10) Patent No.: US 6,835,180 B2
(45) Date of Patent: Dec. 28, 2004

(54) SYSTEM AND METHOD FOR BIOPSY MANAGEMENT

(75) Inventors: James J. Rudnick, Mahwah, NJ (US); Kevin Weadock, Princeton, NJ (US)

(73) Assignee: Ethicon, Inc., Somerville, NJ (US)

( * ) Notice: Subject to any disclaimer, the term of this patent is extended or adjusted under 35 U.S.C. 154(b) by 11 days.

(21) Appl. No.: 10/397,952

(22) Filed: Mar. 26, 2003

(65) Prior Publication Data

US 2003/0212342 A1 Nov. 13, 2003

Related U.S. Application Data

(60) Provisional application No. 60/367,900, filed on Mar. 26, 2002.

(51) Int. Cl.[7] .............................................. A61B 10/00
(52) U.S. Cl. ........................................ 600/562; 606/1
(58) Field of Search ................................ 600/562, 564; 606/1, 167; 604/19, 22; 422/102, 104; 220/500, 502, 505, 507, 526

(56) References Cited

U.S. PATENT DOCUMENTS

| | | | |
|---|---|---|---|
| 749,934 A | 1/1904 | Hollister | |
| 779,338 A | 1/1905 | Williams | |
| 805,948 A | 11/1905 | Evans | |
| 1,334,916 A | 3/1920 | Lukens | |
| 4,574,957 A | 3/1986 | Stead | |
| 4,621,640 A | 11/1986 | Mulhollan et al. | |
| 4,651,753 A | 3/1987 | Lifton | |
| 5,195,533 A | 3/1993 | Chin et al. | |
| 5,234,634 A | 8/1993 | Janoff et al. | |
| 5,524,634 A | 6/1996 | Turkel et al. | |
| 5,526,822 A | 6/1996 | Burbank et al. | |
| 5,573,109 A | 11/1996 | Isacson | |
| 5,601,585 A * | 2/1997 | Banik et al. | 606/180 |
| 5,609,827 A | 3/1997 | Russell et al. | |
| 5,810,744 A | 9/1998 | Chu et al. | |
| 5,823,971 A | 10/1998 | Robinson et al. | |
| 5,928,164 A * | 7/1999 | Burbank et al. | 600/567 |
| 5,980,468 A | 11/1999 | Zimmon | |
| 6,110,127 A * | 8/2000 | Suzuki | 600/565 |
| 6,142,957 A | 11/2000 | Diamond et al. | |
| 6,241,687 B1 * | 6/2001 | Voegele et al. | 600/566 |
| 6,258,327 B1 * | 7/2001 | Tatum | 422/102 |
| 6,322,522 B1 | 11/2001 | Zimmon | |
| 6,330,965 B1 | 12/2001 | Milliman et al. | |
| 6,468,227 B2 * | 10/2002 | Zimmon | 600/564 |
| 6,632,182 B1 * | 10/2003 | Treat | 600/564 |
| 2001/0023353 A1 | 9/2001 | Gordon et al. | |

OTHER PUBLICATIONS

PCT Search Report dated Sep. 4, 2003, for Appn. No. PCT/US03/09365.
International Search Report dated Mar. 29, 2004, for corresponding PCT/US03/09297.

* cited by examiner

Primary Examiner—Charles Marmor

(57) ABSTRACT

A medical specimen carrier, and a method for using the same, is provided wherein the specimen carrier includes a housing having a plurality of compartments therein each capable of holding a tissue specimen. The housing has a length and a cross-section smaller than a cross-section of a surgical port so as to enable it to pass therethrough, and is dimensioned to be placed within the surgical site separate from the surgical port or other surgical instrument. The medical specimen carrier further includes a cover device capable of selectively opening and closing each of the plurality of compartments.

13 Claims, 10 Drawing Sheets

SYSTEM AND METHOD FOR BIOPSY MANAGEMENT

CROSS REFERENCE TO RELATED APPLICATIONS

The present application claims the benefit of earlier filed U.S. provisional patent application No. 60/367,900, filed on Mar. 26, 2002, which is incorporated herein by reference.

FIELD OF THE INVENTION

The present invention relates to a system and method for biopsy management with particular application to minimally invasive surgery, such as endoscopic or laparoscopic surgery. The system and method enables multiple samples to be collected and stored without withdrawal of a biopsy instrument or other element from the surgical site.

BACKGROUND OF THE INVENTION

In the medical world, an increasing number and type of surgeries are being performed using minimally invasive techniques. Typically, these procedures involve making one or more relatively small incisions in the patient in proximity to the surgical target. A cannula or other type of surgical port (hereinafter referred to generally as a "surgical port") is inserted into the patient through the incision to form a conduit through which the surgeon can access the surgical site. The surgeon then performs the entire surgery from the exterior of the patient's body by manipulating surgical devices and instruments through the surgical port.

Minimally invasive procedures are also a desirable means by which to perform biopsies, either independent of or during the course of a minimally invasive surgery. It is often necessary or desirable to take multiple biopsy samples from a given organ or organs. Under these circumstances, individual samples must be captured, stored and their origin recorded to accurately analyze the results.

Many currently known procedures for obtaining biopsy samples involve inserting a biopsy forcep or other harvesting instrument through the surgical port to the desired location, manipulating the instrument to obtain the sample, withdrawing the instrument and sample through the surgical port, transferring the sample to a suitable container, and subsequently repeating the process for each needed sample. As these procedures require repeated removal and reintroduction of the biopsy instrument through the surgical port, they are time consuming, and increase the likelihood of damaging the surgical port. They may also increase the chances for bacterial infection. With each withdrawal also comes the possibility of dislodging the sample from the biopsy instrument. The sample may subsequently be difficult to locate if it drops back into the surgical site. Further, the samples can be dripping fluid and cells as they are withdrawn, potentially "seeding" areas of healthy tissue if diseased cells exits.

In an effort to address some of these problems, some biopsy instruments have been developed that enable multiple samples to be taken without withdrawal of the biopsy instrument from the target site. See, e.g., U.S. Pat. Nos. 4,651,753, 5,526,822, 5,810,744, 5,980,468, 5,524,634, 6,142,957 and 6,322,522. Many of these instruments, however, are not suitable for endoscopic procedures. Others collect the multiple samples external to the body and, therefore, require additional mechanisms to remove the specimen from the target site after each sample is harvested. Many collect multiple samples at or near the target site, but do so in a single container or tube like element that is integral with the biopsy instrument. These devices provide no means for separating and maintaining the integrity of the individual samples. A further drawback is that the samples must still be subsequently transferred to a suitable container or the like for storage and/or transfer to an appropriate site for analysis.

Accordingly, the need exists for an improved system and method for managing a plurality of biopsy samples, particularly for use with minimally invasive surgical techniques.

SUMMARY OF THE INVENTION

The problems and disadvantages associated with the conventional techniques and devices utilized for and during endoscopic surgery are overcome by the present invention, which includes a medical specimen carrier for insertion through a surgical port during a minimally invasive surgical procedure on a patient. The medical specimen carrier includes a housing having a plurality of compartments therein each capable of holding a tissue specimen. The housing has a length and a cross-section smaller than a cross-section of the surgical port so as to enable it to pass therethrough, and is further dimensioned to be placed within the surgical site separate from the surgical port or other surgical instrument. The medical specimen carrier further includes a cover device capable of selectively opening and closing each of said plurality of compartments.

According to another embodiment, the cover device further includes a plurality of cover elements each corresponding to a different one of the plurality of compartments and each capable of being manipulated to open or close the corresponding compartment.

In yet another embodiment, the cover elements are each pivotably coupled to the housing, and in an alternate embodiment the cover elements are slidably engaged with the housing and slidable relative to the housing to selectively open or close the plurality of compartments.

In a further embodiment, each of the plurality of cover elements have a recess therein sized and shaped to receive a tip of a medical instrument. The housing of another embodiment further includes a grasping portion at one end thereof.

Also provided is a method for obtaining a plurality medical specimens during minimally invasive surgery that includes the steps of introducing into a surgical site through a surgical port a medical specimen carrier having a plurality of separate compartments each for receiving a medical specimen therein, positioning the specimen carrier within the surgical site apart from the surgical port or other surgical instrument, obtaining a first medical specimen from the surgical site, and placing the first medical specimen within a first one of the plurality of compartments of the specimen carrier. According to another embodiment, the method further includes the steps of obtaining a second medical specimen from the surgical site, placing the second medical specimen in a second one of the plurality of compartments, and removing the specimen carrier from the surgical site via the surgical port.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION

It should be understood that the embodiments described herein are merely exemplary and that a person skilled in the art may make many variations and modifications without departing from the spirit and scope of the invention as defined in the appended claims. Accordingly, all such variations and modifications are intended to be included within the scope of the invention as defined in the appended claims.

According to the present disclosure, a medical specimen carrier is provided for holding a plurality of medical specimens, such as tissue or biopsy samples, within a surgical site during the course of an endoscopic medical procedure. Although the discussion below will primarily focus on biopsy samples, it is to be understood that the present invention may be used with any procedure in which medical specimens are collected from a patient. The medical specimen carrier is designed to be positioned within the surgical site in the vicinity of the target tissue, but independent of the surgical port or any other instrument being used to perform the procedure.

Figure 1:
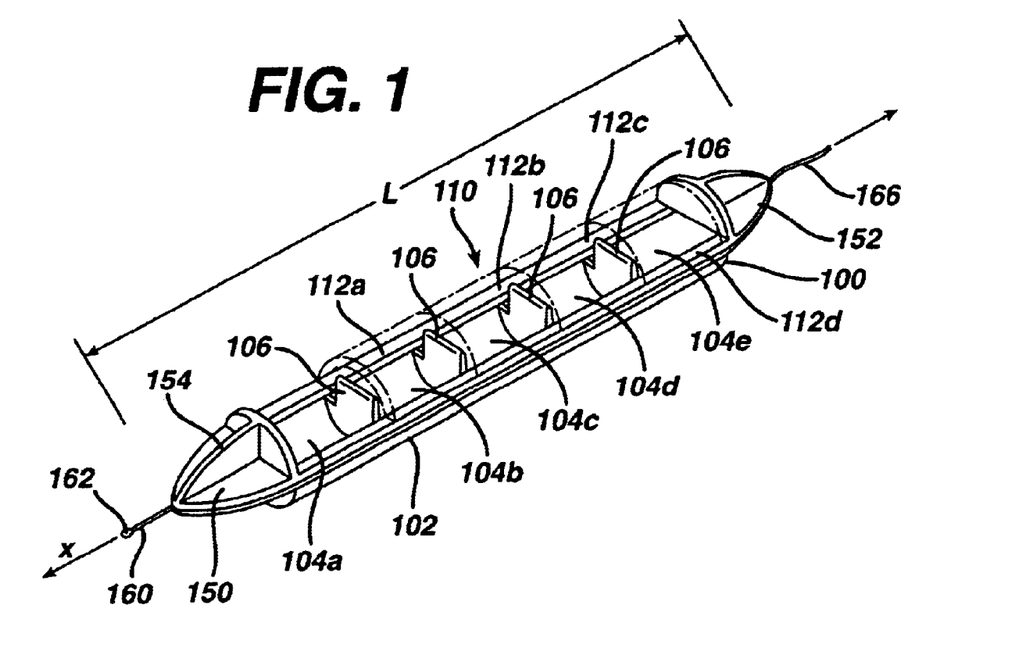
FIG. 1 illustrates one embodiment of a medical specimen carrier according to the present disclosure having a first compartment open for receiving a specimen therein.

One embodiment of a surgical carrier according to the present disclosure is illustrated in FIGS. 1–4. The surgical carrier 100 is substantially cylindrical in overall shape, as illustrated in FIG. 1, and has an outer diameter D that is less than the inner diameter of a surgical port through which the minimally invasive surgery is performed. In a preferred embodiment, the diameter is slightly less than 10 or 12 mm to allow passage through surgical ports with internal diameters of 10 and 12 mm respectively. The length L of the carrier may vary, but should be small enough to both fit into the surgical site, and be manipulated therein without damaging surrounding tissue or organs. In one embodiment, the length L is approximately 11 cm, but could range from less than 5 to greater than 15 cm depending upon the type and number of biopsies to be performed.

Figure 1A:
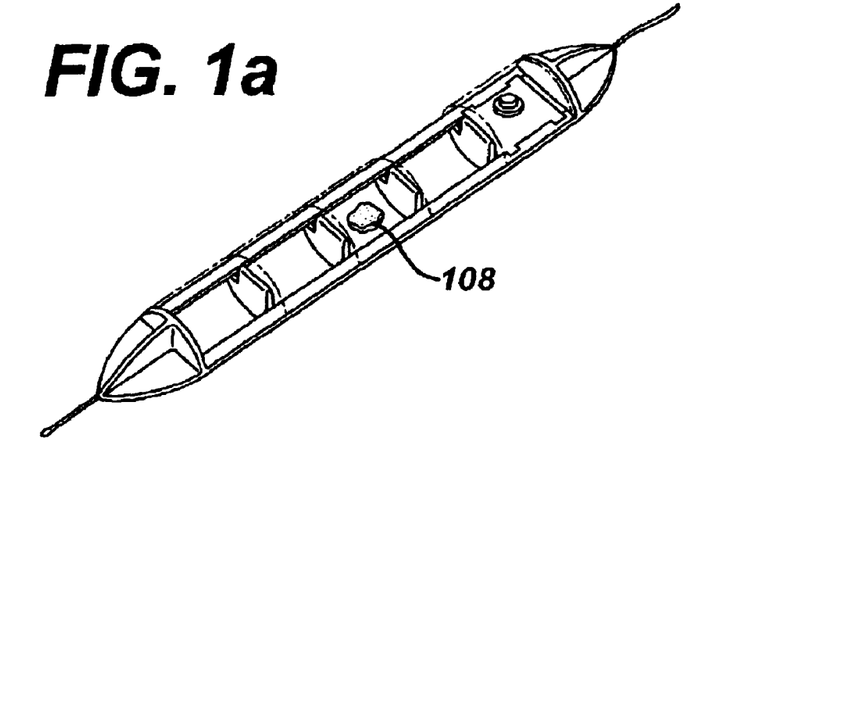
FIG. 1a illustrates a specimen carrier according to the present disclosure having medical specimens therein.
Figure 2:
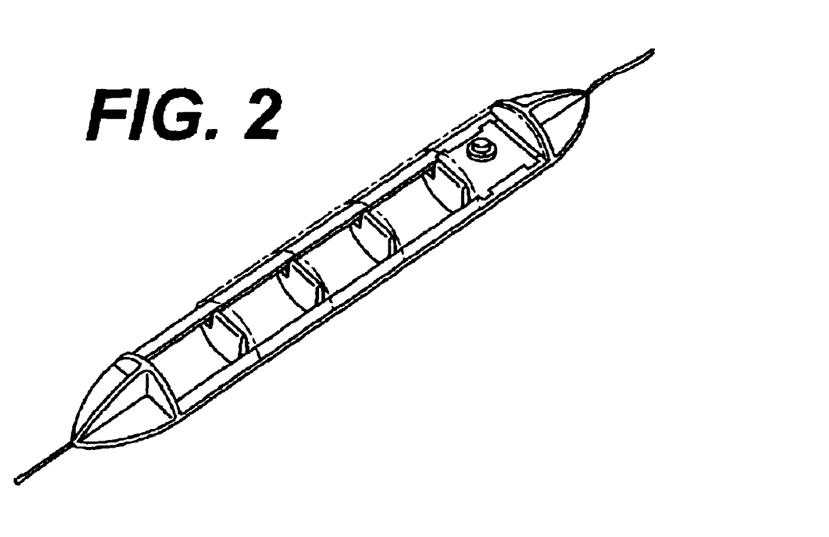
FIG. 2 illustrates the carrier of FIG. 1 with a different compartment open.
Figure 3:
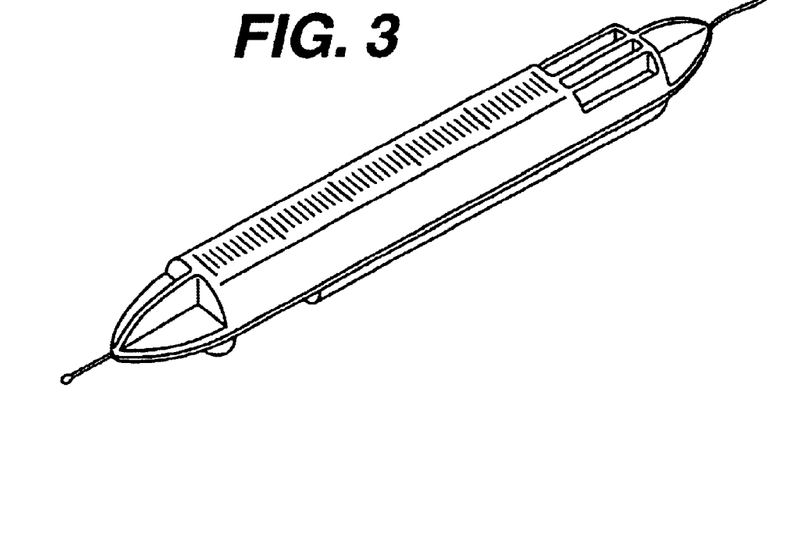
FIG. 3 is a bottom perspective view of the carrier of FIG. 1.

The carrier illustrated in FIG. 1 includes a housing 102 having a plurality of individual compartments 104a–104e. The compartments are separated from one another by divider elements 106, with each compartment being sized and shaped to receive therein a medical specimen 108 (see FIG. 1a) from the surgical site. The carrier also includes a cover device 110 that enables the user to selectively open and close each compartment, to thereby allow a medical specimen to be placed in the compartment and subsequently be protected by closing the compartment. In this manner, multiple medical specimens can be collected, but be maintained separate from one another to maintain their integrity. The cover device further includes a plurality of cover elements 112a–112d each of which are slidably engaged with the housing so as to selectively open or close the compartments. In the embodiment shown in FIG. 1, the specimen carrier has one less cover element than there are compartments, although the extra space need not be a compartment at all. Each cover element is slidable relative to the housing so as to close one or another of two adjacent compartments. For example, cover element 112a is slidable relative to the housing so that it may cover either compartment 104a or 104b. In this manner, during the surgical procedure, a specimen may be placed in compartment 104a, then cover element 112a slid over to cover that compartment (and to open the next compartment 104b), then a specimen placed in compartment 104b, and so on until four specimens have been collected and covered.

Figure 4A:
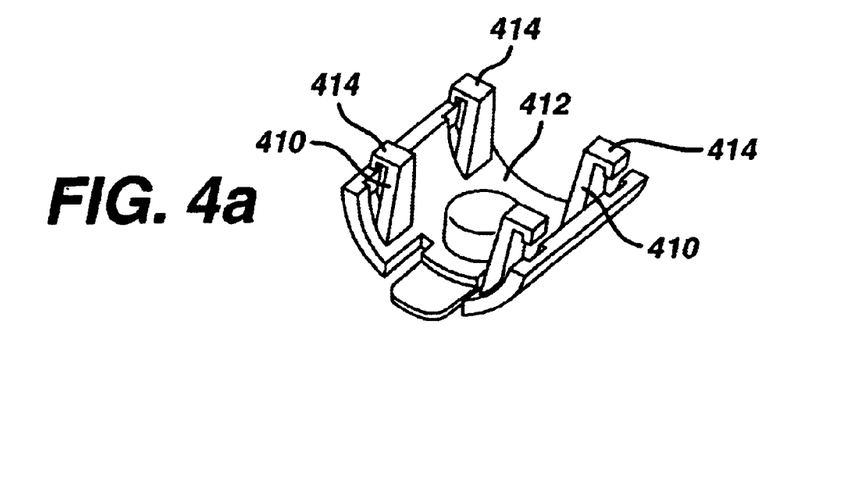
FIGS. 4a and 4b are perspective top and bottom views of a cover element shown in FIG. 1.
Figure 4B:
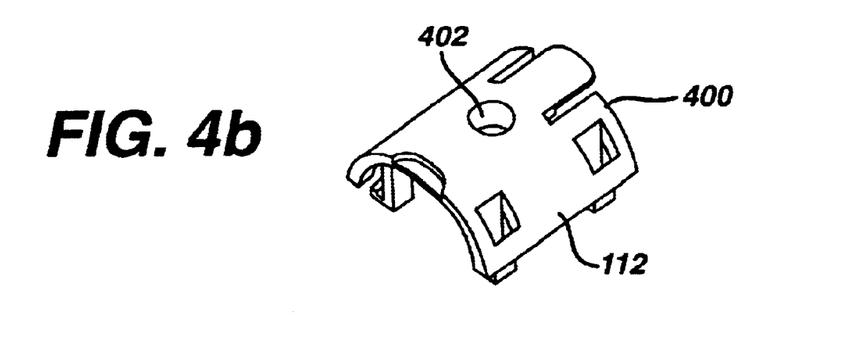
Figure 4C:
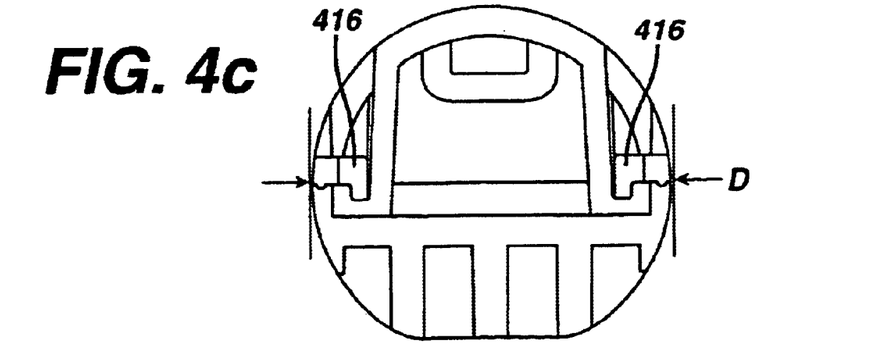
FIG. 4c is a cross-sectional view of the medical specimen carrier of FIG. 1.

The cover elements of the embodiment of FIG. 1 are shown in greater detail in FIGS. 4a–4c. In a preferred embodiment, an outer surface 400 of the cover element 112 has a recess 402 therein. The recess 402 may be sized and shaped to readily receive therein the tip of a surgical instrument, such as scissors or a grasper. Using the surgical instrument within the recess, the user can selectively open and close the desired compartment. This configuration is advantageous in that it allows the specimen carrier to be inserted into the body with one compartment already open, and once a specimen is placed in that first compartment, it can be closed and the subsequent compartment opened with a single action, i.e., simply using a surgical instrument to slide the first cover element over the first compartment, thereby opening the second compartment.

Referring now to FIGS. 4a and 4c, in this embodiment, four projecting elements 410 project outwardly from an inner surface 412 of the cover element. The ends of the projecting elements include tab elements 414 that are configured to engage housing tab elements 416 that project from the housing. The cover tab elements 414 and the housing tab elements 416 engage one another in a manner that allows lateral movement relative to one another in the direction of the length of the specimen carrier (direction x—x in FIG. 1), but substantially prevents movement relative to one another in any other direction.

Referring back to FIG. 1, although the illustrated specimen carrier is substantially cylindrical in overall shape, it includes first and second ends 150, 152 that are configured to readily allow the carrier to be grasped by an endoscopic surgical instrument. In this embodiment, the first and second ends are tapered, and include ridges 154 that can be grasped by the surgical instrument. Various configurations of the first and second ends are possible without departing from the scope of the invention, as will be apparent to those skilled in the art.

A tip 160 may also extend from one end (i.e., 150) of the specimen carrier. The tip may be made of a braided or monofilament suture, and may include a knot or bulbous portion 162 to facilitate grasping with various instruments. The surgical carrier may also include a flexible tether element 166 coupled to one end (i.e., 152). The tether element is long enough so that, when the specimen carrier is positioned in proximity to the surgical site, it extends through the surgical port to the outside of the patient's body, as can be seen in FIGS. 7a–7g. Preferably, the tether element is made of a braided or monofilament suture.

Figure 5A:
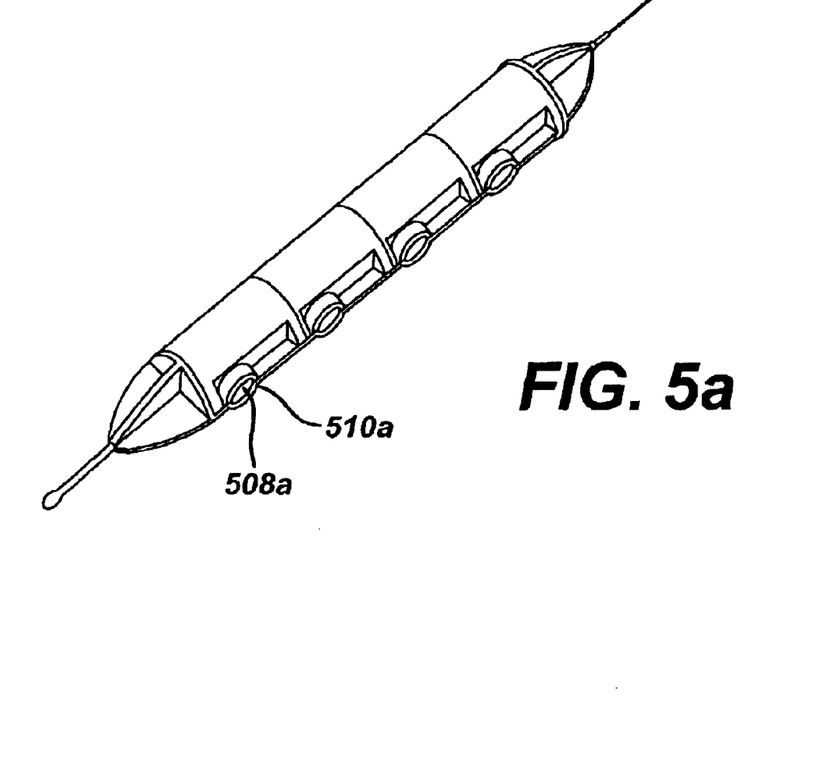
FIG. 5a illustrates another embodiment of a medical specimen carrier according to the present disclosure with all cover elements in a closed position.
Figure 5B:
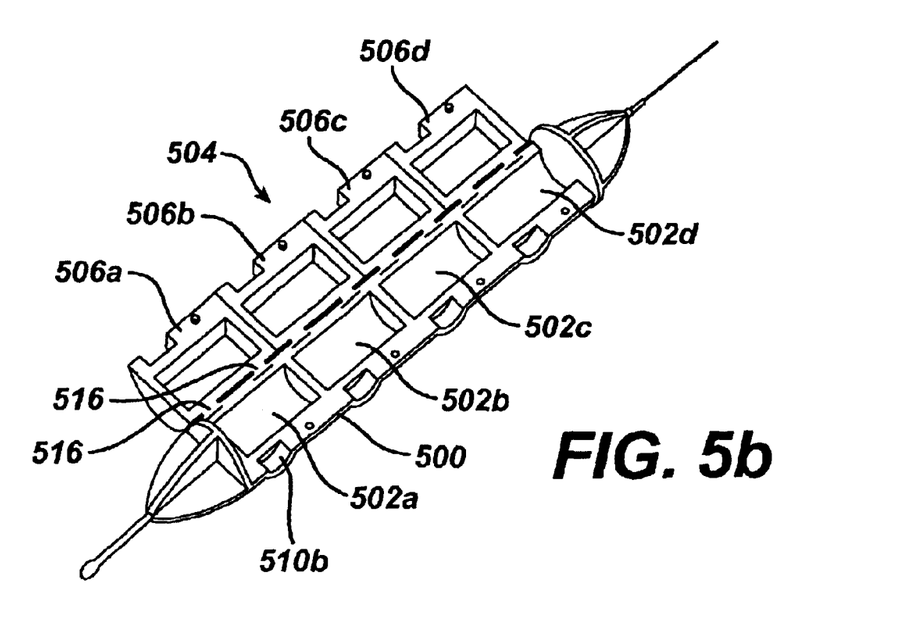
FIG. 5b illustrates the carrier of FIG. 5a with all cover elements in an open position.
Figures 6, 6A:
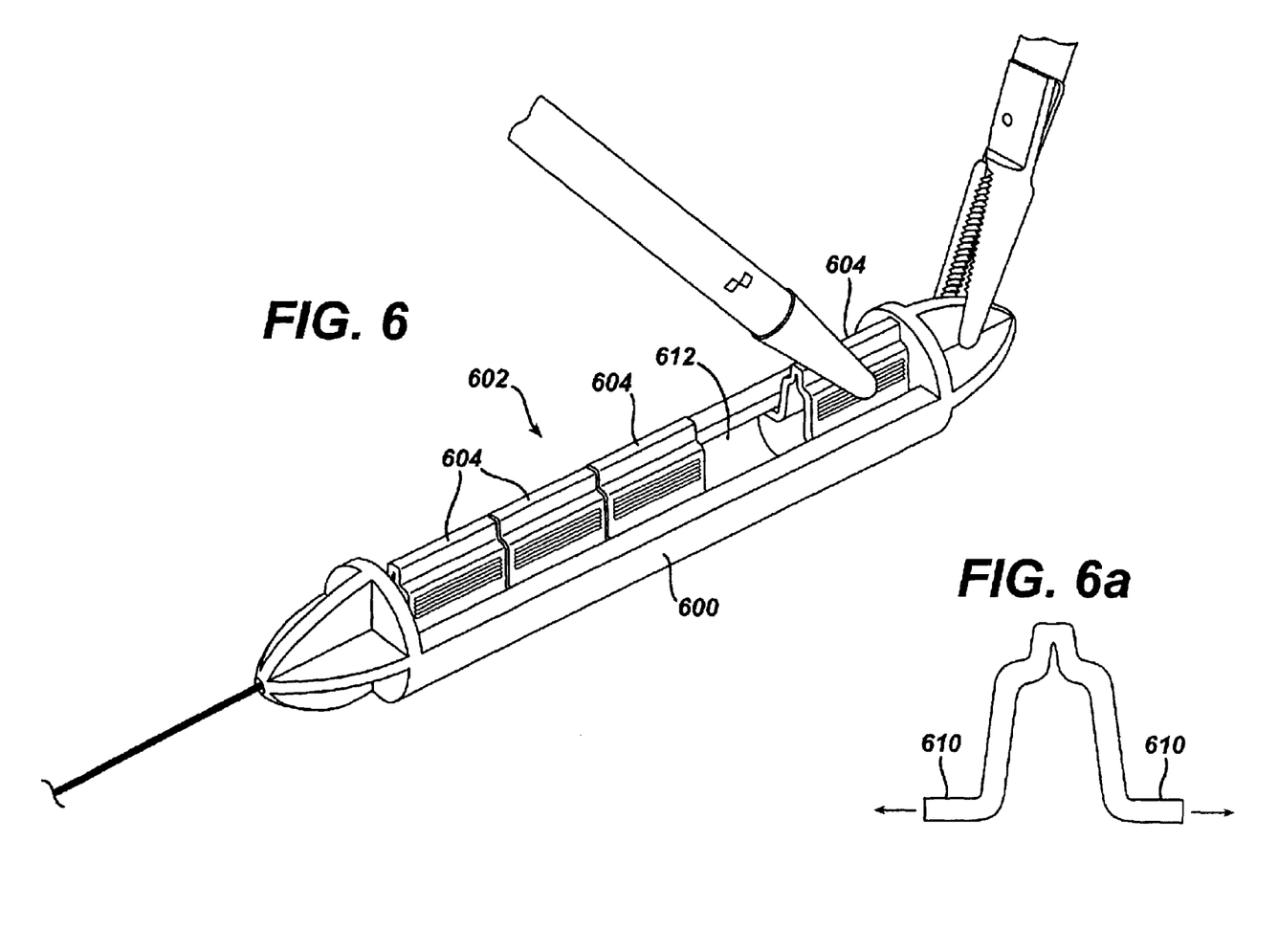
FIG. 6 illustrates yet another embodiment of a medical specimen carrier according to the present disclosure.
FIG. 6a is a cross-sectional view of a cover element shown in FIG. 6.

Other representative embodiments of the present invention are illustrated in FIGS. 5a, 5b and 6. The specimen carrier of FIGS. 5a and 5b includes a housing 500 having four compartments 502a–d and a cover device 504 including four cover elements 506a–d. Each cover element is pivotably coupled to the housing by pivot elements (516), and pivotable relative to the housing between an open position wherein the corresponding compartment is exposed, and a closed position wherein the corresponding compartment is covered. The housing and cover elements are further configured so that, when a cover element is in the closed position (FIG. 5a), a recess (i.e., 508a) exists between the housing and the cover element. The recess is sized and shaped to receive therein the tip of a surgical instrument, such as scissors or a grasper, that can subsequently be manipulated to exert pressure on the opposite sides of the recess (the cover element side 510a and the housing side 510b) to cause the cover element to pivot relative to the housing, thereby opening the compartment. In this manner, each compartment can be opened using an endoscopic surgical instrument.

In yet another embodiment illustrated in FIG. 6, the specimen carrier includes a housing 600 and a cover device 602 including a plurality of cover elements 604 that are slidably engaged with the housing in a manner similar to the embodiment of FIG. 1 described above. Each of the cover elements, however, includes foot portions 610 (see FIG. 6a) that are at least partially positioned within grooves 612 in the housing. The foot portions engage the grooves in such a manner that the cover elements can slide laterally relative to the housing (i.e., using a grasper as shown in FIG. 6), but cannot be disengaged from the housing. In one embodiment, the cover elements may be constructed so that they are biased outwardly in the direction shown by the arrows in FIG. 6a, in which case graspers can be used to pinch together the sides of the cover element sufficiently to slide the cover element laterally within the groove.

Although particular embodiments have been described herein, various other designs for the cover elements are within the scope of the invention and will be apparent to those skilled in the art. The cover elements may incorporate magnets, latches or any other suitable means to maintain the cover in a closed position until the user desires to open it. The cover elements may also be comprised of a transparent material to enable any harvested samples to be viewed while enclosed within the surgical carrier. The surgical carriers described herein may be made of any suitable biocompatible material, such as polypropylene, polyethylene, or any injection molding resin of medical grade.

Figure 7A:
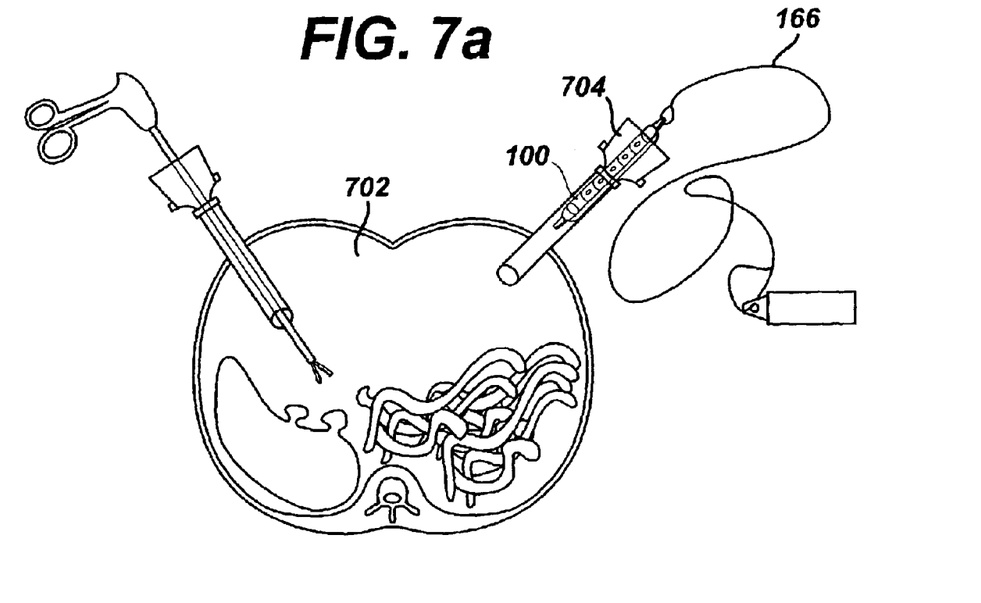
FIGS. 7a–7g illustrate various steps of a method for using a medical specimen carrier according to the present disclosure.
Figure 7B:
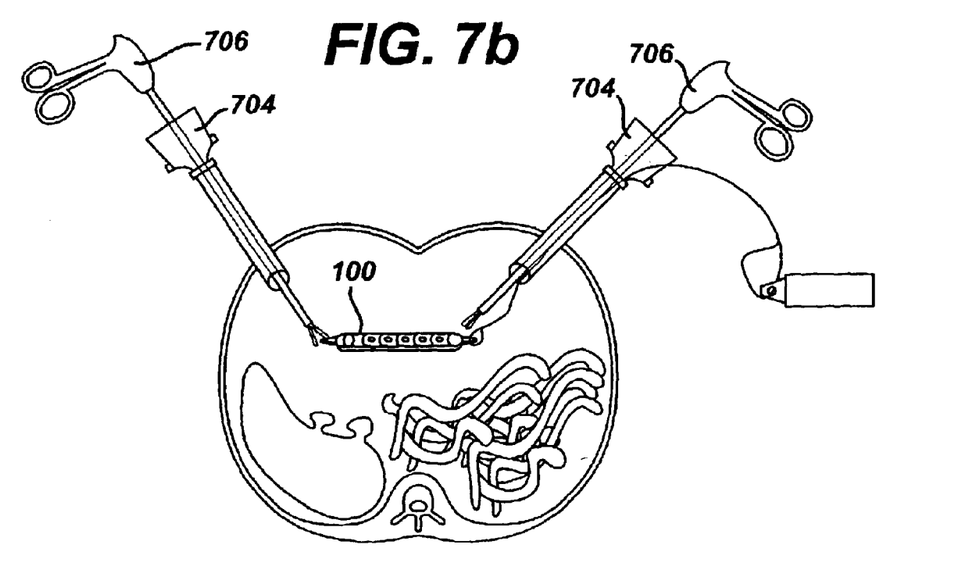
Figure 7C:
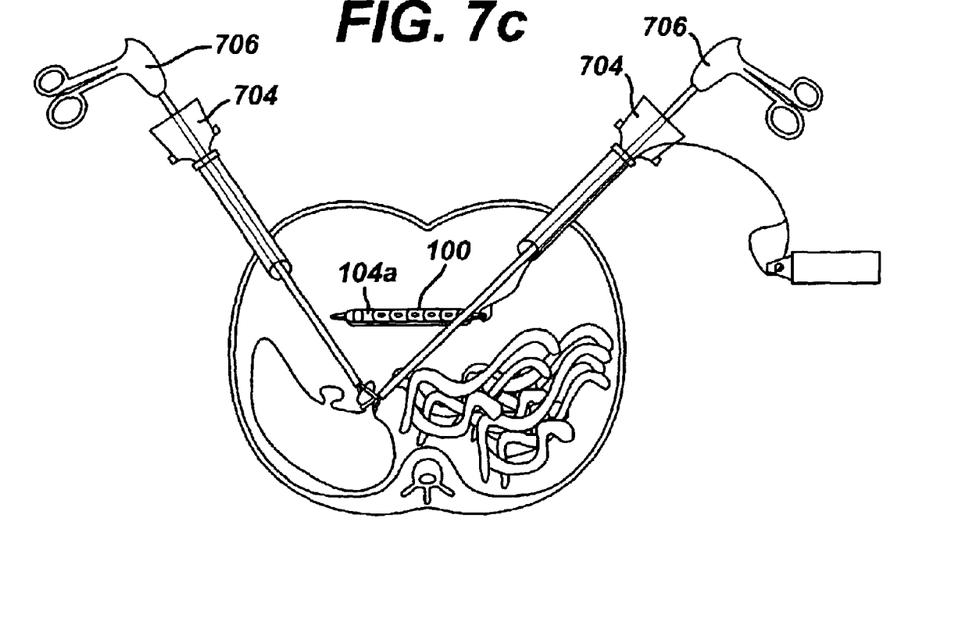
Figure 7D:
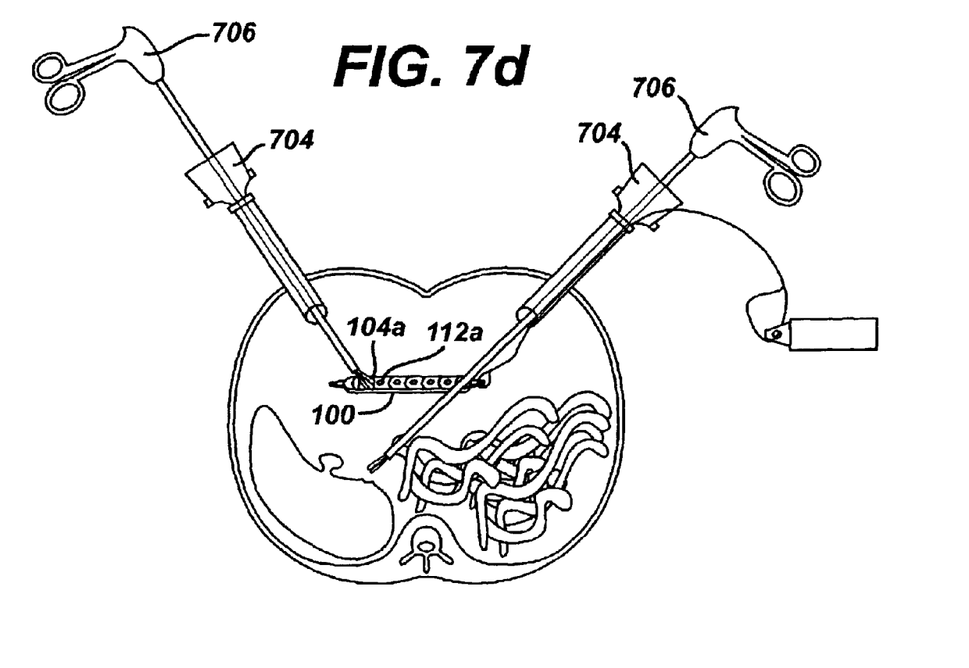
Figure 7E:
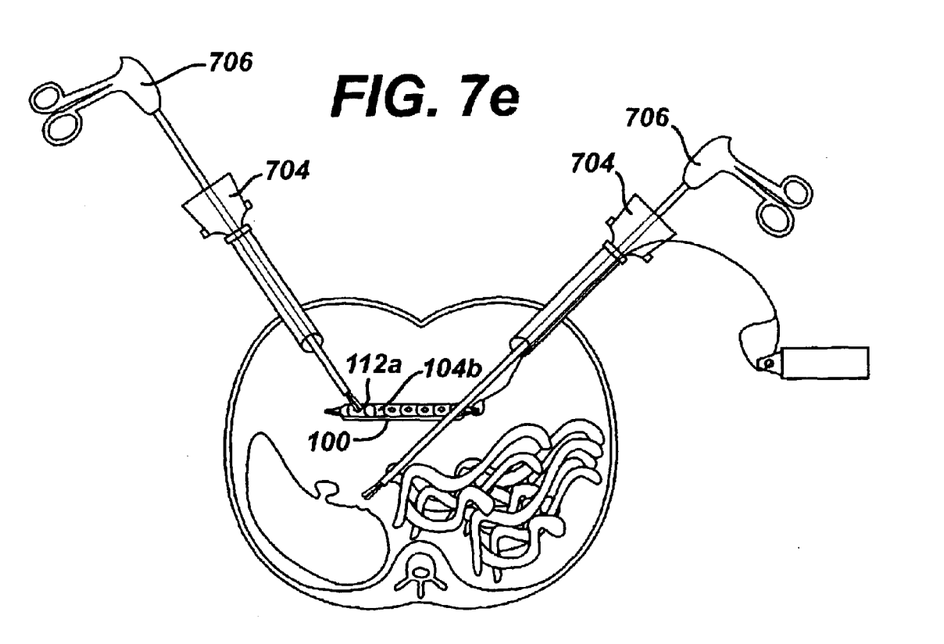
Figure 7F:
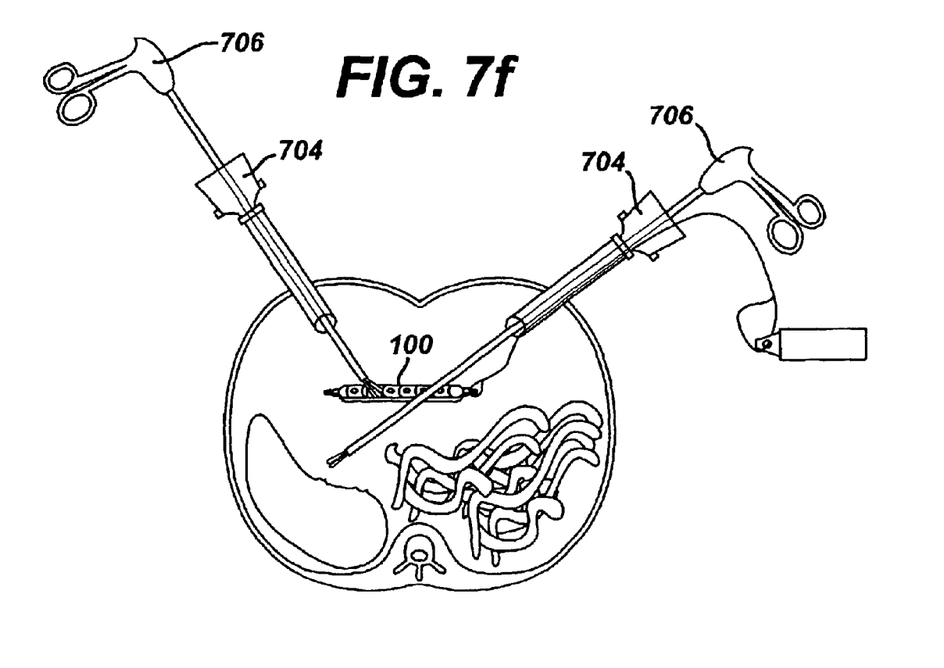
Figure 7G:
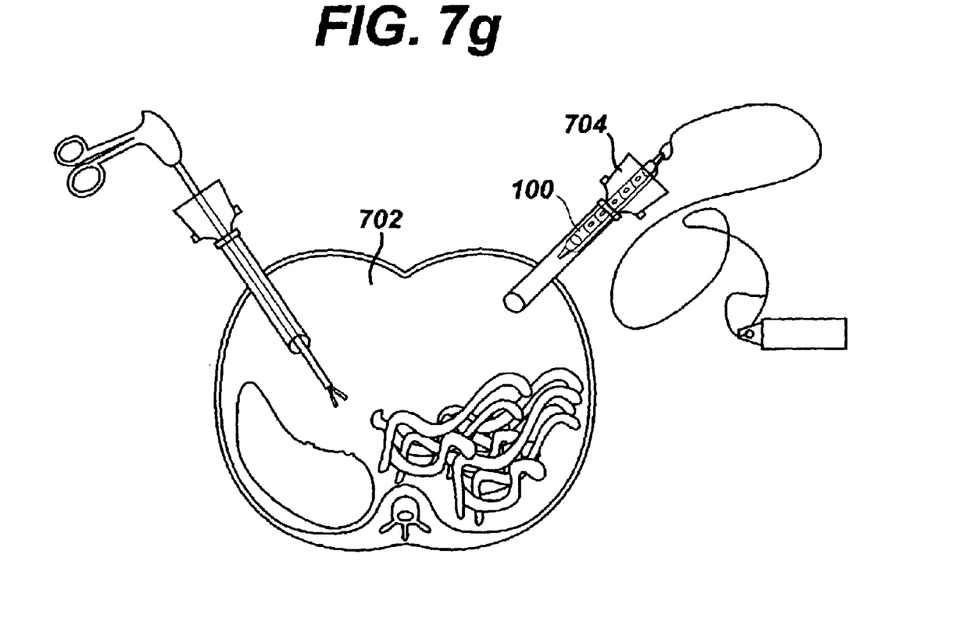
Figure 8:
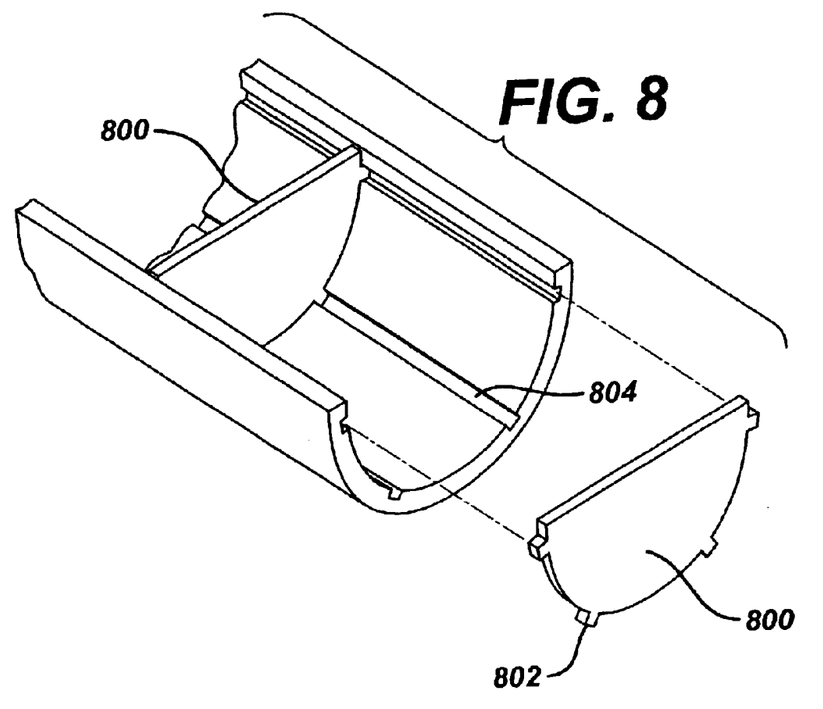
FIG. 8 is a perspective view of a portion of a specimen carrier having a movable divider element.

The surgical carrier may also include divider elements that are removable from the surgical carrier, or otherwise capable of being moved by the user between a first position wherein the divider element separates successive compartments, and a second position wherein the divider element no longer separates the compartments. In this manner, successive compartments can be combined to accommodate larger samples. For example, one or more divider elements may slidably engage vertical grooves in the housing in such a manner that the divider element can be inserted into the groove, or removed from the groove to thereby remove it from the housing. In another embodiment, the divider elements can be pivotably, or otherwise movably mounted to the carrier and movable between the first and second positions described above. Such an embodiment is shown in FIG. 8, wherein the divider element 800 includes one or more projections 802 that are slidably positioned within corresponding horizontal grooves 804 in the housing. The divider element can be slid within the groove until it abuts another divider element, thereby combining the two adjacent compartments. A method for using a surgical carrier according to the present disclosure will now be described in detail with reference to FIGS. 7a–7g. First, the surgical carrier 100 is inserted into the surgical site 702 through a surgical port 704 as shown in FIG. 7a. Once the specimen carrier is inside the surgical site, the necessary surgical instruments 706 are inserted through the cannula(s), as shown in FIG. 7b, and a first specimen is taken, as shown in FIG. 7c. The first specimen is placed into the first compartment 104a of the specimen carrier as shown in FIG. 7d. Next, the first cover element 112a is slid over the first compartment, thereby exposing the second compartment 104b, as shown in FIG. 7e. A second specimen is then taken and placed in the second compartment (FIG. 7f), and the procedure repeated if necessary for the number of specimens needed. When specimen removal is completed and all occupied compartments covered, the specimen carrier is removed from the surgical site by drawing it back up through the surgical port as shown in FIG. 7g. The attached tether can also be used to aid in the withdrawal of the specimen carrier out of the surgical port. The tether is also a reminder that a device carrier is in use and must be withdrawn at the end of the surgery.

The surgical carriers of the present invention may also incorporate various diagnostic or therapeutic features. For example, one or more chambers may contain a tablet, powder, or other material that reacts with the specimen to indicate the presence of a substance, such as an infection or neoplastic tissue. In another embodiment, instead of a separate powder or element, the walls of the chamber could be coated with a diagnostic material, such as an antigen that would bind with a predetermined antibody (i.e., in a virus or tumor) if present in the specimen. A reagent including an antibody-enzyme conjugate could then be introduced (i.e. from another chamber while in situ or introduced after the surgical carrier is removed from the body) which would react with the specimen to generate a visible color if an antibody was bound to the antigen.

One or more chambers may also contain drugs or therapeutic agents in any form, or a device containing such drugs or agents (i.e. a sponge) that could be used for localized treatment of the biopsy harvest site. For example, the chamber could contain a material to help reduce inflammation, bleeding, infection or the like at the harvest site.

It will be apparent from the foregoing, where particular forms of the invention have been illustrated and described, that various modifications can be made without departing from the spirit and scope of the invention. Accordingly, it is not intended that the invention be limited, except as by the appended claims.

What is claimed is:

1. A medical specimen carrier for insertion through a surgical port during a minimally invasive surgical procedure on a patient, comprising:

a housing having a plurality of compartments therein each capable of holding a tissue specimen, the housing having a length and a cross-section smaller than a cross-section of said surgical port so as to enable the housing to pass therethrough, and being dimensioned to be placed within a surgical site within the patient separate from the surgical port or other surgical instrument; and a cover device capable of selectively opening and closing each of said plurality of compartments.

2. The specimen carrier according to claim 1, wherein the cover device further comprises a plurality of cover elements each corresponding to a different one of the plurality of compartments and each capable of being manipulated to open or close the corresponding compartment.

3. The specimen carrier according to claim 2, wherein the plurality of cover elements are each pivotably coupled to the housing.

4. The specimen carrier according to claim 1, wherein the specimen carrier is substantially cylindrical in overall shape.

5. The specimen carrier according to claim 1, wherein the cover device further comprises a plurality of cover elements slidably engaged with the housing and slidable relative to the housing to selectively open or close the plurality of compartments.

6. The specimen carrier according to claim 5, wherein each of the plurality of cover elements have a recess therein sized and shaped to receive a tip of a medical instrument.

7. The specimen carrier according to claim 1, the housing further comprising a grasping portion at one end thereof.

8. The specimen carrier according to claim 1, further comprising divider elements positioned between successive compartments, wherein at least one of the divider elements is movable between a first position in which it separates the successive compartments, and a second position in which it does not separate the successive compartments.

9. The specimen carrier according to claim 8, wherein the at least one divider element is removable from the specimen carrier.

10. The specimen carrier according to claim 8, wherein the at least one divider element is movably coupled to the housing.

11. A method for obtaining a plurality medical specimens during minimally invasive surgery comprising the steps of:

introducing into a surgical site within a patient through a surgical port a medical specimen carrier having a plurality of separate compartments each for receiving a medical specimen therein;

positioning the specimen carrier within the surgical site apart from the surgical port or other surgical instrument;

obtaining a first medical specimen from the surgical site; and placing the first medical specimen within a first one of the plurality of compartments of the specimen carrier.

12. The method according to claim 11, further comprising the steps of:

obtaining a second medical specimen from the surgical site;

placing the second medical specimen in a second one of the plurality of compartments; and removing the specimen carrier from the surgical site via the surgical port.

13. The method according to claim 12, further comprising the steps of:

following the first placing step, manipulating a cover device of the specimen carrier to close the first compartment; and following the second placing step, manipulating the cover device to close the second compartment.

* * * * *